United States Patent [19]

Ahmad et al.

[11] Patent Number: 5,252,213
[45] Date of Patent: Oct. 12, 1993

[54] DRY DIALYSATE COMPOSITION

[75] Inventors: Suhail Ahmad, Seattle; James J. Cole, Arlington; William Jensen, Seattle, all of Wash.

[73] Assignee: University of Washington, Seattle, Wash.

[21] Appl. No.: 612,214

[22] Filed: Nov. 9, 1990

Related U.S. Application Data

[62] Division of Ser. No. 368,665, Jun. 20, 1989, abandoned.

[51] Int. Cl.$^5$ ............................................. B01D 61/26
[52] U.S. Cl. .................................. 210/542; 210/646; 252/1
[58] Field of Search ............... 210/96.1, 96.2, 206, 210/321.6, 321.71, 321.72–321.81, 424, 541, 542, 646; 252/1, 363.5, 183.16, 190; 424/677, 678, 679, 680, 681

[56] References Cited

U.S. PATENT DOCUMENTS

| | | | |
|---|---|---|---|
| 3,962,075 | 6/1976 | Fialkoff et al. | 210/321.75 |
| 4,326,955 | 4/1982 | Babb et al. | 210/638 |
| 4,614,648 | 9/1986 | Bru | 252/183.16 |
| 4,655,941 | 4/1987 | Suzuki | 210/96.2 |
| 4,690,772 | 9/1987 | Tell et al. | 252/106 |
| 4,734,198 | 3/1988 | Harm et al. | 210/647 |
| 4,756,838 | 7/1988 | Veltman | 210/647 |
| 4,812,239 | 3/1989* | Mills et al. | 210/96.2 |
| 4,968,420 | 11/1990 | Mills et al. | 210/96.2 |
| 5,071,558 | 12/1990 | Itob | 210/542 |

FOREIGN PATENT DOCUMENTS 57-88116  6/1982  Japan ..................................... 424/678

*Primary Examiner*—Robert A. Dawson
*Assistant Examiner*—Sun Uk Kim
*Attorney, Agent, or Firm*—Seed and Berry

[57] ABSTRACT

There is disclosed an automated hemodialysis filtration system comprising one or a plurality of the following improvements, including a supply-regulated pump, an inverted drip chamber, a filtrate system communicating with a hemofilter and comprising a filtrate reservoir, a filter pump and pressure sensors, and a means for adding dry pellets to water to form the dialysate.

7 Claims, 5 Drawing Sheets

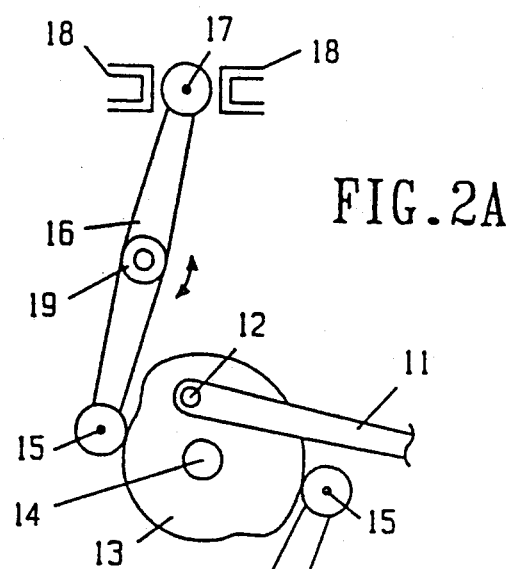
FIG.2A
FIG.2B
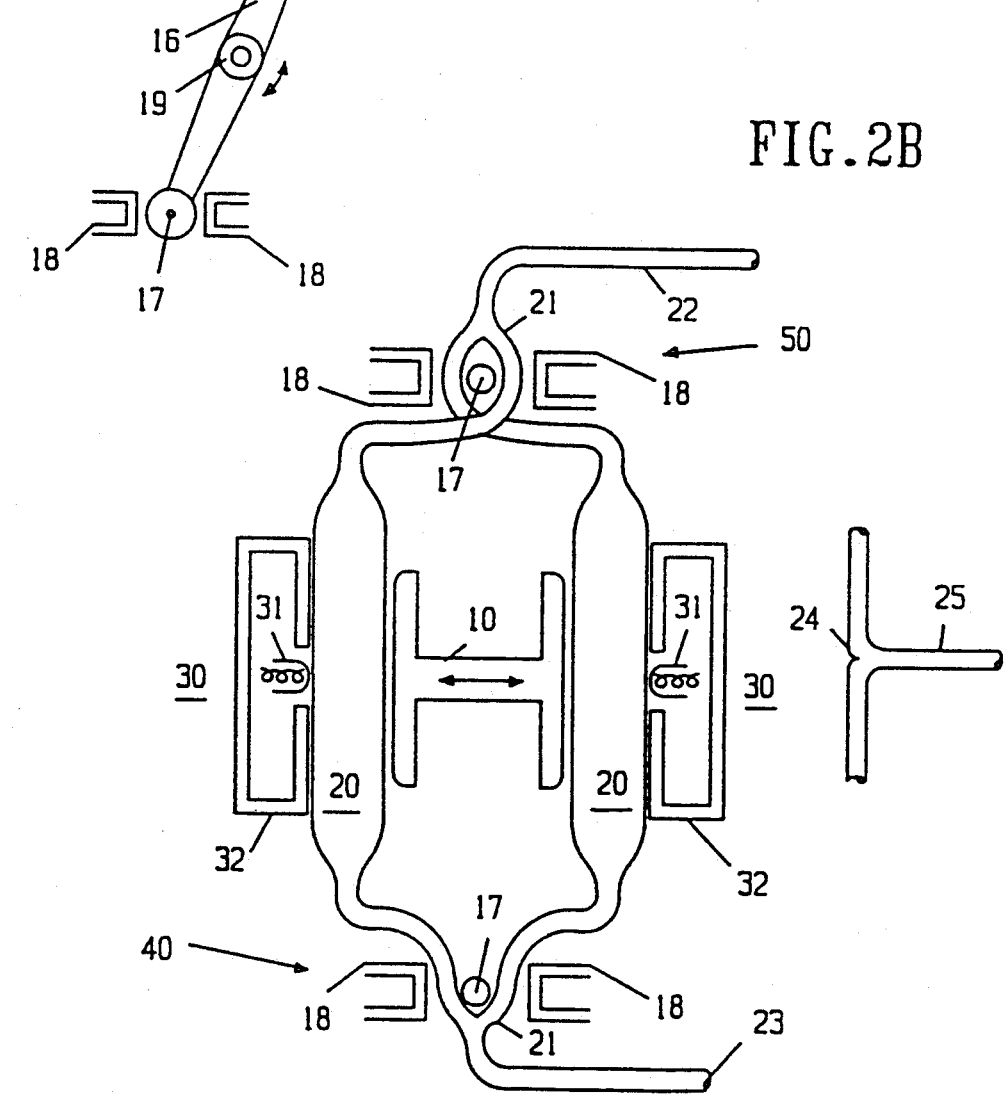

RECIRCULATION TIME (BLEACH), MINUTES.
(FLOW RATE, 200 ml/min, 0.5%)

DRY DIALYSATE COMPOSITION

CROSS REFERENCE TO RELATED APPLICATION

This application is a divisional application to Ser. No. 368,665, filed Jun. 20, 1989, abandoned.

TECHNICAL FIELD OF THE INVENTION

The present invention relates to an automated hemodialysis-filtration system that enables monitoring of the patient and adjustments of the dialysis system according to the changing needs of the patient without the constant vigilance of an assistant. The automated hemodialysis-filtration system utilizes conventional hemodialyzers and hemofilters and adds improvements to the dialysis system, including a supply-regulated blood pump, an automated inverted drip chamber to automatically remove air, and a filtrate system communicating to provide a source of sterile intravenous replacement fluids. These components comprise an integrated design which enables automated dialysis machine processing, automated testing of hemodialyzer and hemofilter in the blood circuit, and reuse of pathways conducting blood and dialysate fluid. The present invention also includes an automated dialysate system comprising dry chemicals of dialysate to mix with water to form the dialysate on-line, without the need of liquid concentrates and proportional pumping systems.

BACKGROUND OF THE INVENTION

In the early 1960s, long-term hemodialysis was introduced for the treatment of irreversible kidney failure. Early in the evolution of this procedure, it was recognized that self-treatment in the home offered important advantages over treatment provided in a dialysis facility. These advantages include recognition that treatment at home could be more cost-effective than care in a dialysis clinic or facility, and the belief that self-care at home would provide a better, more independent lifestyle since the patient could control scheduling of treatment and other important aspects of the therapeutic process.

Hemodialysis treatment is employed as a therapeutic measure when a patient's kidneys no longer perform their blood purifying function because of disease or traumatic removal. Kidney failure results in the accumulation of toxic waste in the patient's blood and eventual death from uremic poisoning, unless the waste material is removed by some artificial means. In hemodialysis, the patient's blood is circulated on one side of a membrane contained within a hemodialyzer (i.e., artificial kidney). The membrane has pores of microscopic size through which waste products from the blood pass. The pores are, however, too small to permit blood cells and proteins to leave the body. A dialysis fluid (dialysate) is circulated on the other side of the hemodialyzer membrane to remove the waste products.

Most kidney failure patients require dialysis treatments three times weekly. Thus hemodialysis treatment requires a significant time commitment by each patient. One attempt to shorten each treatment has been made with high efficiency hemodialysis such as high-flux hemodialysis. High-flux hemodialysis increases the efficiency of hemodialysis by increasing blood flow to the maximum rate possible and by using high-efficiency hemodialyzers. High-flux hemodialysis requires accurate control of filtrate removal rates from the patient, and thus is only able to be conducted with special machines under the careful guidance of skilled medical personnel and is rarely performed in the home. Another example of high efficiency hemodialysis is hemodiafiltration. Hemodiafiltration is a combination of hemodialysis and hemofiltration.

The use of a dialysis machine at home requires the presence of a trained helper to assist with the preparation of the hemodialyzer and associated apparatus both before and after each hemodialysis treatment. The helper usually must remain vigilant throughout the therapeutic process to monitor all of the systems of the hemodialysis machine. It is difficult for the patient to adequately and effectively monitor all of the systems, because a drop in blood pressure, for example, may leave the patient physically unable to respond.

The advantages of home dialysis treatment include important scheduling and lifestyle benefits. These real benefits should have made this form of treatment extremely popular. However, home hemodialysis has failed to achieve the popularity originally envisioned. This is due to several interrelated factors.

(1) The safety of the home dialysis procedure is perceived by patients to be inadequate. For example, small air bubbles may collect in the blood circuit of the system. These must be manually removed by the patient or the helper to prevent their passage into the body via the venous line. The passing of air bubbles into the body could be a life-threatening event.

(2) There is confusion by many patients about dialysis machine operation. This is especially true with regard to adjustment of the blood pump to a rate sufficient for effective treatment yet not so fast that the pumping rate exceeds the ability of the body to provide blood to the pump. If the pump rate is too fast, an alarm sounds, necessitating a corrective action sequence which many patients view as complicated and confusing.

(3) Excessive work is required to perform dialysis treatment. Time is required to do step-by-step pre- and post-dialysis machine processing, setup and teardown of the hemodialyzer and blood circuit as well as all the necessary small steps incidental to treatment. The time necessary to prepare each treatment is estimated to be 1 hour to 1½ hours. This time is in addition to the 3 to 5 hours of actual dialysis treatment that is performed three times each week. For many patients, this additional time is an unacceptable burden. For example, the setup activities include the removal of sterilizing agents and testing for their removal, attachment of sterile saline, and start-up of the apparatus, including an assessment of proper functioning. After dialysis treatment, the apparatus must be flushed and either a replacement blood circuit tubing set installed or steps taken to reuse the blood circuit tubing. Reusing the blood circuit involves cleaning, flushing, testing of circuit integrity, and filling with a sterilizing agent. The dialysis machine must be completely cleaned and sterilized weekly. The weekly maintenance and sterilizing requires 3 to 4 hours.

(4) The responsibility for home treatment is shared between the patient and the helper (e.g., spouse). It is widely recognized that patient independence and sole responsibility for care promote rehabilitation and a sense of well-being. However, for many home dialysis patients, the combination of time requirements to prepare for treatment and the attendant uncertainties about proper use of the dialysis machine often cause significant reliance on the helper and a strong relationship of interdependence. This adds to the stress experienced by the patient and by the patient's family, especially when the spouse serves as the helper.

(5) The dialysis machine is intrusive in the home. The size of contemporary dialysis machines makes it difficult to remove them from visibility to family and friends. Thus, the machine serves as a constant reminder of the patient's affliction and dependency. Coupled to this problem is a requirement that large volumes of dialysate concentrate must be stored for use with the machine. The concentrate is a solution of inorganic and organic chemicals which are proportionally mixed with water by the machine to produce the dialysis rinsing solution, called "dialysate," which flushes the machine during treatment. Concentrate volume increasingly is a limiting factor to home treatment due to the widening trend toward apartment-sized dwellings with limited living space.

The contemporary dialysis machine has a blood circuit comprising a blood pump, a hemodialyzer, and usually one or two drip chambers. During treatment, blood is drawn from the patient usually through a needle inserted into a blood vessel in the arm, pumped through the hemodialyzer and drip chamber, and then returned to the patient via a second needle. In the hemodialyzer, the blood passes through one or more chambers, each enclosed by a permeable membrane. A dialysate fluid is simultaneously pumped through the hemodialyzer on the opposite side of this membrane. The toxic components in the blood which are the result of kidney failure pass across the membrane from the blood to the dialysate and are carried away, thereby purifying the blood. The dialysate solution is generally manufactured by mixing treated water with a concentrated solution of several inorganic salts.

In contemporary dialysis systems, usually the blood tubing set is replaced after each treatment. This is due to protein accumulation on the inner walls, especially within the drip chamber, which makes it difficult to clean, and because of physical wear of the walls by the roller blood pump. This wear is increased with improperly adjusted roller blood pumps and may release small fragments of the tubing into the blood stream as microemboli. This complication is greater with silicone rubber tubing. The use of a pumping system that can accurately and reliably pump blood in the blood circuit without significant damage to the wall of the tubing will reduce physical wear on the tubing and hazard from microemboli, and require less frequent replacement. Therefore, there is a need in the art for such an external pump for the blood circuit of a dialysis system.

The blood pump for contemporary dialysis systems is a rotary pump that is set for a specified pumping rate of blood from the patient. The pump rate is usually set below the normal blood output of the patient. The patient's blood flow may drop during treatment below the rate set on the blood pump, which will trigger an alarm and stoppage of the blood pump. Therefore, there is a need in the art for a dialysis blood pump whose pump rate adjusts to the changing output rate of the patient so as to allow a faster treatment time and avoidance of alarms (machine stoppage) due to a drop in patient blood supply.

Another problem for contemporary dialysis systems is the cost and complexity of apparatus required to accurately measure fluid loss during dialysis treatment. Measurements of fluid loss usually are accomplished by weight loss determinations before and after treatment. Some investigators have tried to make better fluid loss determinations by monitoring weight throughout the treatment process. This procedure requires a special weighing bed or chair. Therefore, there is a need in the art for a simple and accurate means to measure fluid loss during treatment.

Further still, a limitation of contemporary dialysis systems is the inability to automatically respond to a fall in patient blood pressure. Technology is available to continuously monitor a patient's blood pressure. However, there is a need in the art to be able to automatically and therapeutically respond to a change in a patient's blood pressure, without relying upon the eventual arrival of help.

Accordingly, there is a need in the art to revise the contemporary dialysis machine and its accompanying fluids to better automate the treatment process so as to allow less vigilance, to expedite or automate the treatment process so that the setup and teardown times can be reduced, and to reduce the physical size of the dialysis system, including the concentrates.

SUMMARY OF THE INVENTION

The problems described above are solved by an automated hemodialysis-filtration system comprising a supply-regulated blood pump, a hemofilter, a hemodialyzer, and an inverted drip chamber, wherein the blood pump, hemofilter, hemodialyzer, and inverted drip chamber communicate to form a blood circuit, and a filtrate system communicating with the hemofilter and the blood circuit and comprising a filtrate reservoir, a filtrate pump, and pressure sensors. The automated hemodialysis-filtration system automates both the pre and post-treatment processing steps and most monitoring and control functions during the treatment process. Although the primary focus of the present invention is toward home treatment, several of the subsystems and component parts can be used in hospital and treatment centers with beneficial improvement over existing apparatus and techniques.

The automated hemodialysis-filtration system incorporates several novel features, including the supply-regulated blood pump, the inverted drip chamber, the filtrate system, and the dialysate on-line production system. The inventive automated hemodialysis-filtration system can include one or a plurality of the novel components described herein, including the supply-regulated blood pump, the filtrate system, the inverted drip chamber, and the dialysate on-line production systems.

The supply-regulated pump comprises a fill chamber, a means for compressing the fill chamber, a fill chamber sensor, an inlet pinch valve, and an outlet pinch valve, wherein a liquid fills the fill chamber, the fill chamber sensor directs the inlet pinch valve to close and the outlet pinch valve to open, and the means to compress the fill chamber pumps the liquid through the system. Thus the input to the supply-regulated pump controls the rate at which the liquid is pumped.

Preferably, the supply-regulated pump is controlled by the blood output of a patient, wherein the fill chamber is filled by the supply (arterial) line from the patient. The supply-regulated pump, when used as a blood pump for a dialysis machine, can function as a single-needle or double-needle blood pumping system when the pump has a single fill chamber. When operating with dual fill chambers, the supply-regulated blood pump operates as a double-needle blood pumping system. Moreover, it is a novel feature of the supply-regulated pump to be convertible as a blood pump for use with either single-needle or double-needle hemodialysis systems.

Furthermore, the pumping action of the supply-regulated pump, when used as a blood pump for the blood circuit in a hemodialysis system, does not cause as much abrasion or other damage to the wall of the blood tubing because the blood pumping is caused by compressing the fill chamber rather than by having a roller run along a length of tubing. Thus the supply-regulated pump allows for less frequent replacement of blood circuit tubing sets for hemodialysis.

As an additional benefit, the supply-regulated pump, when used as a hemodialysis blood circuit pump, does not require an alarm when the patient's blood outdoes put drops within a preset range, because the pumping rate automatically slows to accommodate the patient's reduced output. If the pumping rate drops below a preset value, the system will alert the patient. Conversely, when the patient's blood output increases, the pump rate increases to allow for faster dialysis treatment.

The filtrate system communicates with a hemofilter in the blood circuit and comprises a filtrate reservoir, a filtrate pump, and pressure sensors. The filtrate system stores a plasma ultrafiltrate from the hemofilter in the reservoir for later use if needed. The filtrate pump controls the plasma ultrafiltrate removal rate and volume pumped from the blood in accordance with the desired rate and total weight loss or fluid loss during a dialysis treatment. The plasma ultrafiltrate is collected in the filtrate reservoir. When the desired volume loss has been achieved, the filtrate pump stops and no further ultrafiltration need occur.

The filtrate system is preprogrammed to collect a specified volume of a plasma ultrafiltrate according to the weight loss or fluid loss needs of the patient. This accurate measure of actual fluid loss is determined by either the volume pumped by the filtrate pump or the volume in the filtrate reservoir, or both. Moreover, should the patient's blood pressure drop during dialysis treatment, the plasma ultrafiltrate stored in the filtrate reservoir is available for return to the patient. This is accomplished by reversing the flow of the filtrate pump.

At the conclusion of a dialysis treatment, the plasma ultrafiltrate stored in the reservoir can be used to flush the blood circuit and to return blood to the patient, thus automating the process and eliminating the need for sterile saline intravenous solution. Preferably, the return line of the filtrate system to the blood circuit communicates with the inverted drip chamber.

An air-capture reservoir comprises an inverted drip chamber with a tapered upper end to minimize blood/air interaction. An air sensor is located on or within the inverted drip chamber to detect air bubbles. Preferably, the inverted drip chamber further comprises a means for adding an anticoagulant to the blood circuit. The air bubbles that are trapped within the inverted drip chamber are automatically removed when sensed by the air sensor. The air bubbles preferably are removed to the filtrate reservoir via the filtrate return line. This system avoids the monitoring by the nurse or helper to constantly and manually remove air bubbles trapped in the drip chamber.

The inverted, tapered upper end of the drip chamber along with rapid removal of air minimizes the air/blood surface interaction to minimize fibrin ring deposits. Moreover, the use of the drip chamber as a point of entry for the anticoagulant avoids the buildup of fibrin ring that often occurs from air/blood interaction.

Examples of anticoagulants include, for example, heparin, heparin fragments, prostacyclin, citrate salts and combinations thereof. The preferred anticoagulant is heparin.

Further still, the present invention comprises a dialysate production system utilizing dry chemical pellets or tablets, wherein the pellet or tablet contains an acid or acids, a base or bases, and salts, with the proviso that the acid component be separated from the base component. The pellets are added to mixing chambers containing treated water to form the dialysate. The mixed dialysate from the chambers flows into the dialysate circuit through the hemodialyzer and/or hemofilter. Preferably, the acid component is citric acid, and this forms an effervescence upon contact with water and other chemicals to facilitate the solution of the dry chemical into the dialysate and maintains a pH below 7.4. Moreover, the more acid pH prevents calcium carbonate from forming an insoluble precipitate in the aqueous solution.

BRIEF DESCRIPTION OF THE DRAWINGS

FIGS. 2a and 2b are a schematic of a supply-regulated pump that can operate with either a single-needle dialysis system (24 and 25) or a double-needle system (22 and 23). A dual chambered system is illustrated in FIG. 2b. Liquid or blood flows in through the inlet pinch valve (40) and fills a fill chamber (20) while the outlet pinch valve (50) is closed. A fill chamber sensor (30) comprising a spring-loaded plunger (31) in a rigid housing (32) senses when each fill chamber is filled. When the fill chamber sensor determines that the fill chamber is filled, the compressing means (10), such as a moving pressure shoe, constricts the fill chamber, forcing liquid out through the outlet pinch valve. The inlet pinch valve (40) and the outlet pinch valve (50) are opened and closed when the cam travel (13) reaches the valve reset point on the cam.

Figure 1:
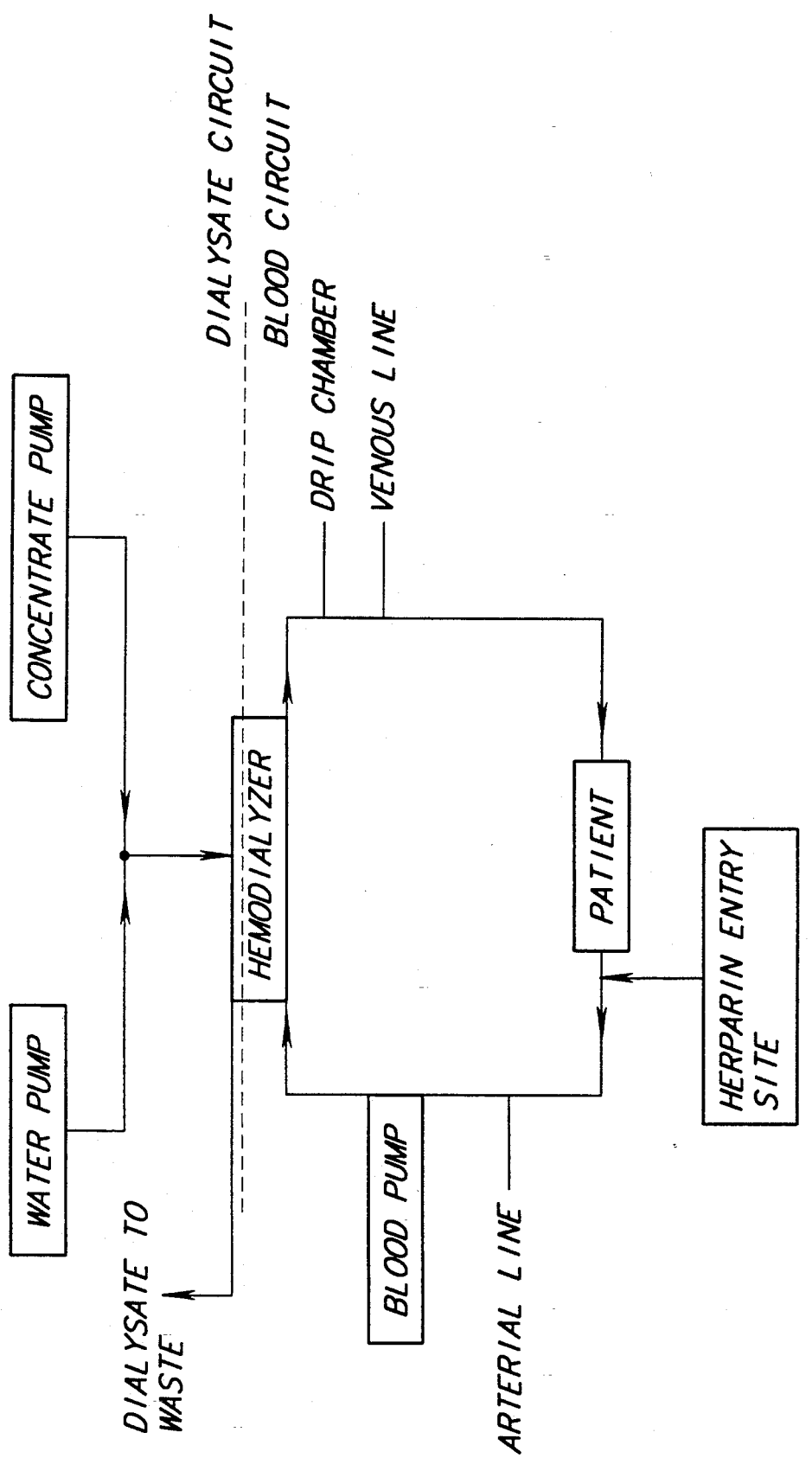
FIG. 1 shows a schematic of the main components in a traditional hemodialysis system. An "arterial" line runs from the patient to the blood pump tubing and then to the hemodialyzer. The blood continues on through to the drip chamber in the "venous" line and back into the patient. This forms the blood circuit. The dialysate circuit is formed by mixing the dialysate concentrate with treated water and passing the mixture on the other side of the hemodialyzer membrane and then continuing out to waste.

The dual-chambered, supply-regulated pump will have one chamber compressed while the other chamber is open. There is a natural recovery of the compressed tube to fill to the limits of its chamber. The natural recovery occurs with the inlet pinch valve open so as to create a slight vacuum to draw blood into the chamber.

In FIGS. 2a and 2b, power is supplied to the compressing means (10) via a motor-driven shaft (14) supported on bearings. The shaft (14) turns a cam (13) carrying a crankpin (12). The crankpin (12) operates a connecting rod (11), which, in turn, operates the oscillating compressing means (10) in FIG. 2b. The cam (13) contacts two cam followers (15) on the ends of levers (16) which pivot about their center points (19). At the opposite ends of the levers (16) are pinch pins (17)

which compress the flexible tubing against fixed blocks (18).

The compressing means (10) alternately compresses two expandable chambers (20) against rigid housings (30). The chambers function in conjunction with the 5 pinch valves (17 and 18) to pump fluid. In the event that neither chamber is able to fill, the plunger (31) will move with the collapsing chamber wall to operate a switch which will interrupt the motion of the motor turning the drive shaft (14).

The two chambers (20) are connected to the ingress (23) and egress (22) tubes by tee connectors (21). If a single tube (25) for both ingress and egress is desired (e.g., single-needle dialysis system), then the ingress and egress tubes are connected to each other by a tee (24) and a single chamber is used.

Figure 3:
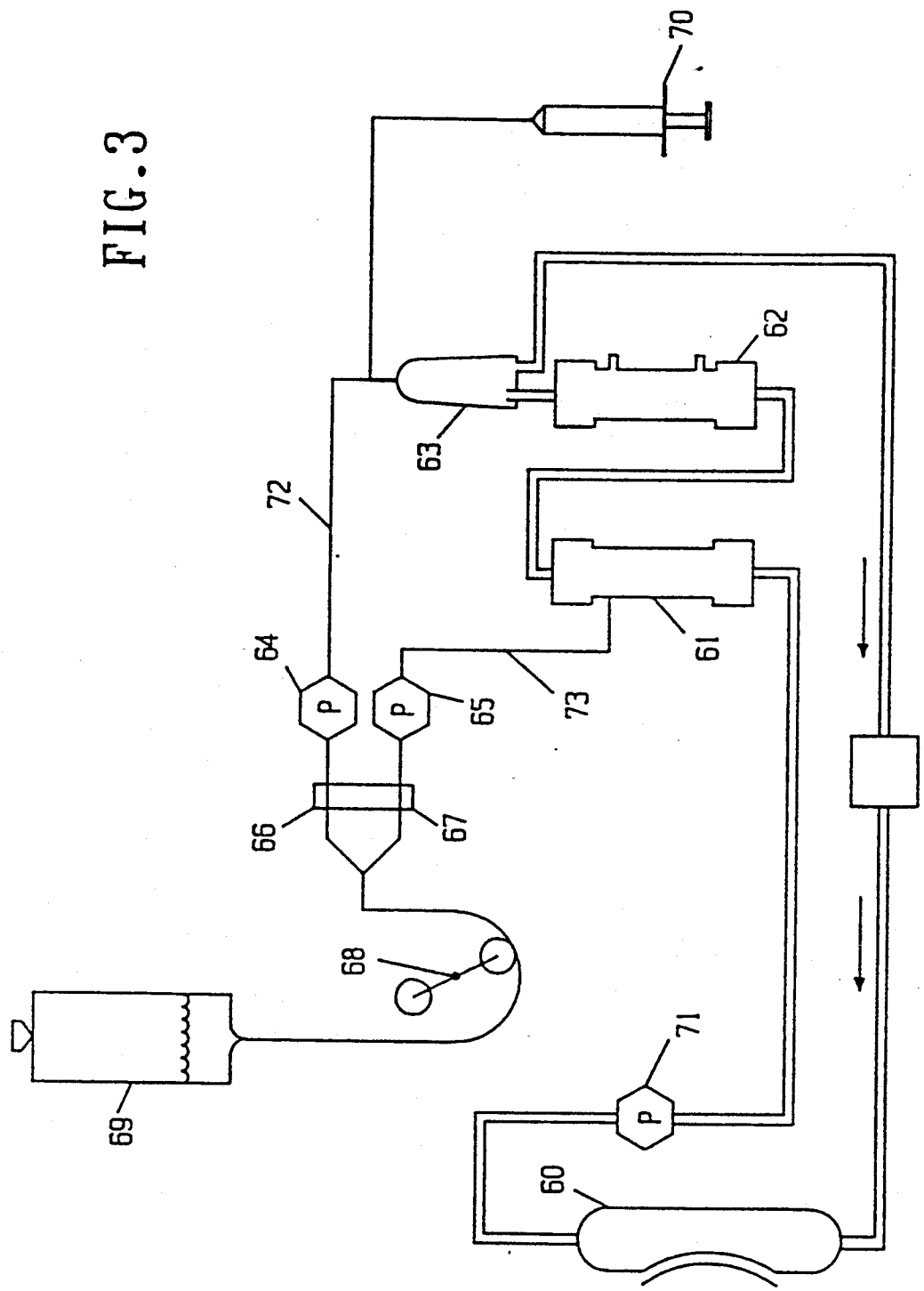

FIG. 3 illustrates an example of a blood circuit and a filtrate system. The supply-regulated pump (60) delivers blood from the patient to the blood circuit. The filtrate system communicates with a hemofilter (61) and a hemodialyzer (62) via an inverted drip chamber (63) and a filtrate access line (72). The filtrate system draws off a plasma ultrafiltrate from the hemofilter through a ultrafiltrate access line (73), a pressure sensor (65) and a valve (67), pumping the plasma ultrafiltrate into the filtrate reservoir (69) with a filtrate pump (68). If no further plasma ultrafiltrate is desired, the valve (67) will close and the pump (68) will stop. Should the blood pressure drop in the patient or should plasma ultrafiltrate be needed to return blood to the patient and/or wash out the blood circuit system at the conclusion of dialysis, then the plasma ultrafiltrate in the filtrate reservoir is returned to the blood circuit by having the valve (66) open, and via pressure sensor (64) and filtrate access line (72) through the inverted drip chamber (63), and into the blood circuit.

Alternatively, plasma ultrafiltrate can be returned to the blood circuit via valve (67) and pressure sensor (65) via the filtrate access line (73) into the hemofilter (61). Additionally, an anticoagulant (70) is added to the blood circuit via the inverted drip chamber (63). The presence of the anticoagulant avoids blood clots in the extracorporeal circuit, and its introduction through the drip chamber helps to avoid the formation of a fibrin ring in the drip chamber. This facilitates cleaning and reduces the frequency of changing the tubing set.

Figure 4:
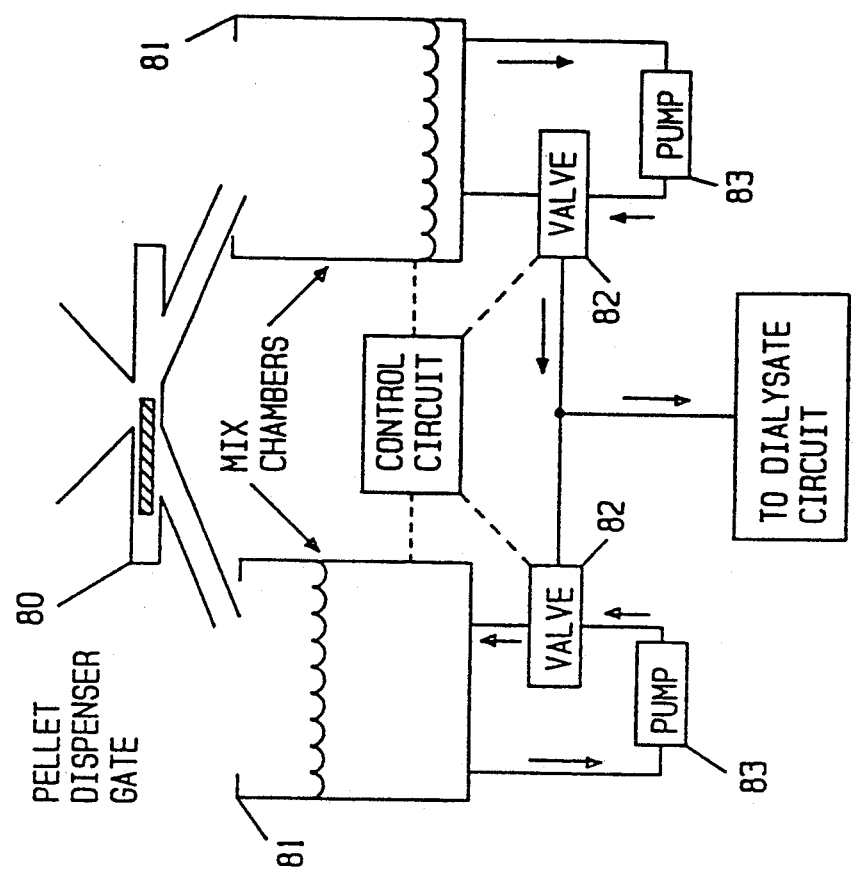

FIG. 4 shows a schematic of a dialysate production system utilizing dry chemical pellets. The pellets are dropped into the pellet dispenser gate (80) and then added to one of the two mix chambers (81). The pump (83) circulates water in the mix chamber to dissolve the pellet. Preferably, the presence of citric acid in the pellet regulates the pH of the water/chemical mixture (i.e., dialysate) to pH 7.4 or below to prevent calcium carbonate precipitate from forming. The valve (82) controls the addition of the dialysate in the mix chamber to enter the dialysate circuit. The dialysate production system allows the direct addition of chemical to water to produce dialysate without the need of a concentrate proportioning pump.

Figure 5:
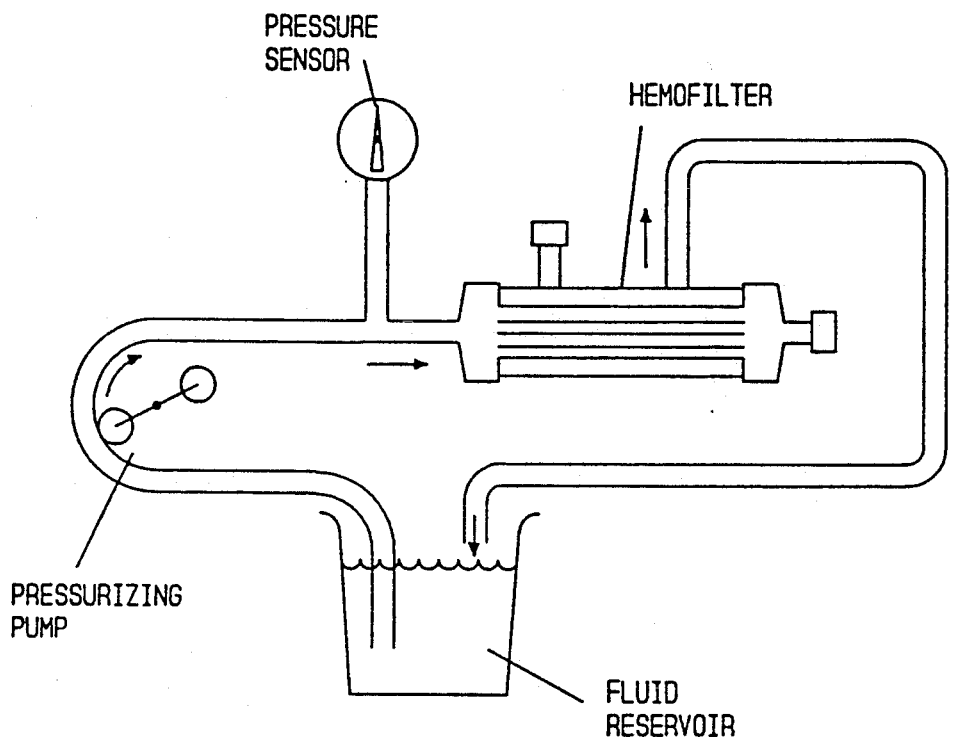

FIG. 5 illustrates a hemofilter membrane integrity testing apparatus which is described in Example 5. The pressurizing pump pumps fluid from the fluid reservoir to one side of a hemofilter membrane. The outlet is capped. Fluid that moves to the other side of the membrane is returned to the fluid reservoir. Membrane permeability was measured by measuring the inlet (arterial) pressure with a pressure sensor and recording the time required for the pressure to drop to its lowest stable level. Membrane integrity was measured by determining air pressure loss after pressurizing the arterial side of a hemofilter membrane.

Figure 6:
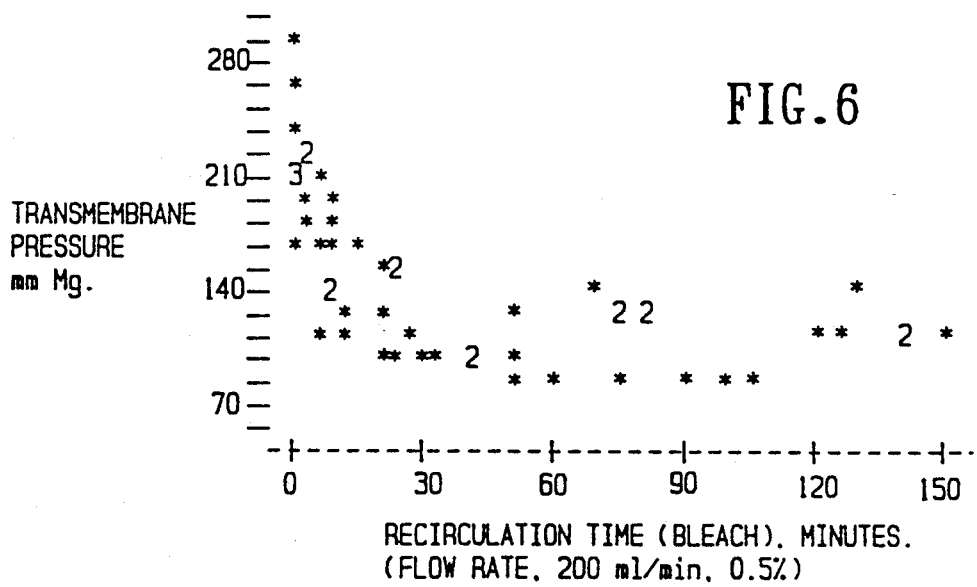

FIG. 6 illustrates a graph of test results from Example 5 showing the effectiveness of hemofilter cleaning with 0.5% sodium hypochlorite (bleach). Low transmembrane pressure reflects cleaned membrane and this occurred after 40 minutes of exposure to bleach.

DETAILED DESCRIPTION OF THE INVENTION

The present invention comprises an automated hemodialysis-filtration system with one or a plurality of novel components described herein. One of the components is a supply-regulated pump. The supply-regulated pump can be used as a blood pump in either a single-needle dialysis system or a double-needle dialysis system. The supply-regulated pump can further be used for a variety of other applications where source pressure control is needed, such as for organ perfusion, other blood pumping applications, and chemical, scientific, and industrial applications (e.g., pumping of cement, liquid and semisolid wastes, and roofing tar). An advantage of the inventive pump is that the pressure and flow characteristics of the pulsatile delivery can be altered to suit the particular use requirements. Biological and medical uses for the pump will especially benefit from the similarity between the flow from the inventive pump and the natural pulsations generated by the heart.

Presently used blood pumps in dialysis systems operate on the principle of tube compression by rollers which sweep the blood forward within the tubing. For dialysis treatment, the operator adjusts the pump speed to a rate believed appropriate to the individual patient. The operator then relies on an adjustable pressure monitor to sound an alarm when disproportion develops between available blood flow from the patient and pump delivery rate. In actual practice, the pump rates are often adjusted below those which could be achieved, in order to reduce the frequency of alarms. This is because, when an alarm sounds, the pump is automatically stopped, which, overall, will result in a loss of dialysis treatment time. Alarms can also be caused by patient movement, low blood pressure or technical problems with blood access. Since the dialysis effectiveness is dependent upon the rate of blood flow, the lowering of the blood flow rate by slowing the roller rate of the blood pump has the effect of prolonging treatment time.

The supply-regulated pump permits optimum blood flow without the occurrence of disruptive alarms and disruption of the treatment process. The pump, as shown in FIG. 2, comprises a fill chamber (20), a means for compressing the fill chamber (10), a fill chamber sensor (30), an inlet pinch valve (40), and an outlet pinch valve (50), wherein a liquid fills the fill chamber until the inlet pinch valve closes and the outlet pinch valve opens. The pumping cycle continues as the compressing means compresses the fill chamber until the inlet pinch valve closes and the outlet pinch valve opens. The compressing means then withdraws from the fill chamber, allowing it to fill with liquid, completing the cycle. This cycle continues to repeat as long as the fill chamber sensor detects that the chamber is filling. If the sensor detects collapse of the fill chamber wall, then the cycle is slowed or interrupted until such time as the chamber fills.

Preferably, the supply-regulated pump is used as a blood pump to optimize the blood flow available from the patient. The supply-regulated pump, when used as a dialysis blood circuit pump, avoids the occurrence of alarms and system shutdowns by adjusting to changing patient conditions affecting blood supply. Utilizing this principle of controlling the maximum vacuum in the chamber makes it possible to achieve the highest flows possible within the constraints imposed by the status of the patient.

As the fill chamber fills, it expands. This expansion is monitored by the fill chamber sensor. Preferably, the fill chamber sensor comprises a spring-loaded follower in a rigid housing means. Alternatively, the sensor can be a pressure transducer. The fill chamber sensor controls the operation of the compressing means, which is the pump drive. Preferably, the compressing means is a moving pressure shoe, much like a piston. The fill chamber sensor also controls the openings and closings of the outlet pinch valve and the inlet pinch valve. Valves may be internal or external. Externally acting valves are the preferred method for blood-containing tubing. It is important that the valves control liquid movement from the outside of tubing.

If the supply of fluid is slowed, or if there is an obstruction of the blood line or vascular access line, the fill chamber fills with blood at a slower rate. Similarly, the pump slows to accommodate the changed condition. Likewise, if more fluid, such as blood, can be delivered to the fill chamber by the patient due to improved supply, as indicated by a more rapid chamber fill rate, the pump speed increases as it senses the increased blood flow rate from the patient. Fluid flow is thus optimized to the unique circumstances of the individual patient as those circumstances change. The supply-regulated pump thus overcomes the major weaknesses inherent in the presently used pump systems, such as an obligatory adjustment to slower flow rates, the anxiety producing alarms, and the necessity of frequent interruptions or adjustments of the dialysis apparatus by the patient or the helper.

An additional feature of the supply-regulated pump is that it can easily be converted to pump blood by either the double-needle or the single-needle dialysis techniques. In current practice, there are two methods of providing blood flow for dialysis treatment. The more common method employs two needles in the patient's blood vessels, one serving to withdraw blood from the patient and the second serving to return the dialyzed blood back to the patient. An alternative method, called "single-needle dialysis," employs one intravenous needle and an external valve and pump controller to regulate alternate blood withdrawal from the patient and its return. For example, a single-needle system is described in U.S. Pat. No. 3,756,234, the disclosure of which is incorporated by reference herein. Other single-needle systems are available. The advantage of the single-needle system is the elimination of one of the two venipunctures required for double-needle dialysis. The current single-needle and double-needle pumping systems are not interchangeable and must be purchased separately at additional expense.

In an alternative embodiment, the supply regulated pump may comprise a plurality of chambers to allow a more constant flow of fluid. When used in a dialysis system, the supply regulated blood pump for the blood circuit with a plurality of chambers creates a steadier, less pulsed fluid flow.

An alternative description of the supply-regulated pump comprises a vessel (i.e., fill chamber) with flexible walls, flexible-walled infeed and discharge tubes connected to the vessel, infeed and discharge valves, a compression means, an operating means, and a control means. There may also be a second vessel with second flexible-walled infeed and discharge tubes, infeed and discharge valves, and a control means. The compression means compresses the vessel into the discharge tube, whose valve is open. The compression means has a return movement during which the vessel is permitted to expand. When there are two vessels, the beginning of the compression movement in one vessel is the beginning of the return movement in the other vessel. Similarly, the infeed and discharge valves are in opposite positions for each vessel.

The operating means alternatively opens and closes the valves and alternately moves the compression means in the compression and return movements. This discharges liquid from the vessel during the compression movement with the vessel's discharge valve open and the infeed valve closed. The operating means then permits the vessel to refill with the liquid during the return movement. The return movement has the infeed valve open and the discharge valve closed.

The control means controls the operating means. The control means starts the compression means to compress the vessel (i.e., compression movement) when the vessel is filled to a predetermined extent with liquid supplied through the infeed tube. Therefore, the operation of the supply-regulated pump is controlled by the supply of liquid to the vessel.

Preferably, the liquid is blood and the valves are external pinch valves that do not have any obstructions within the flexible-walled tubing that could form a blood clot, thrombus, or embolus.

The supply-regulated blood pump can be provided as a dual-needle system which is readily converted to single-needle operation by bypassing one pump chamber and redirecting the blood tubing in the existing control valves. This is illustrated in FIG. 2. No additional apparatus is required and this conversion requires only a short time to effect the change. Therefore, a unique feature of the supply-regulated blood pump is its ability to be convertible to either a single-needle or a double-needle dialysis system.

An additional benefit of the supply-regulated blood pump for use in a dialysis system is that no shearing action is imparted to the fill chambers by the pump mechanism. Thus, the tubing life can be extended significantly and the risk of microemboli is significantly reduced. The currently used roller pumps cause shearing action on the pump tubing, necessitating frequent replacement of the tubing systems. The ability to extend tubing life by means of the supply-regulated blood pump can effect a time and cost reduction for dialysis treatments because replacement of the tubing due to wear will be necessary only at significantly extended intervals. For example, a single-chamber, supply-regulated blood pump was constructed which is similar to the pump shown in FIG. 2. Liquid was pumped through the pump over an extended period of time to simulate the equivalence of two years of hemodialysis treatment with a single patient, assuming three treatments weekly. The test results showed no deterioration (e.g., outer wall abrasion) of the tubing over a simulated two-year period.

Another improvement of the automated hemodialysis-filtration system includes a filtrate system. The filtrate system communicates with the blood circuit at two points; through a hemofilter and preferably through the inverted drip chamber. The filtrate system comprises a filtrate reservoir, filtrate pump, and pressure sensor. The hemofilter (e.g., Amicon Diafilter TM) is currently used in dialysis systems and comprises a porous membrane through which a plasma-like filtrate fluid (plasma ultrafiltrate) can be withdrawn from the patient's blood. Any hemodialyzer with high permeability membrane, for example, a Fresenius F6 or F8, can be used in place of a hemofilter. Usually, molecules that pass through the hemofilter have an upper limit molecular weight from about 15,000 to about 55,000 daltons, depending upon the specific hemofilter or hemodialyzer used. Thus, "hemofilter," as used herein, refers to any filtration device that ultrafilters plasma to form an ultrafiltrate. "Hemodialyzer," as used herein, refers to any device which allows ultrafiltration and diffusion of molecules between blood and a supplied dialysate fluid. A filtrate pump is interposed between the hemofilter and an ultrafiltrate fluid reservoir. The drip chamber may also be included in the novel filtrate system wherein filtrate may be returned from the filtrate reservoir to the blood circuit via the drip chamber.

During the operation of a dialysis system containing the inventive filtrate system, plasma ultrafiltrate is drawn from the hemofilter by the filtrate pump and stored in the filtrate reservoir. If intravenous fluid is needed to replace plasma losses during treatment, for example, if the patient's blood pressure suddenly drops, the collected ultrafiltrate can be returned to the patient by reversing the filtrate pump, thereby delivering fluid from the reservoir to the patient via the blood circuit. Points of reentry into the blood circuit include a hemofilter, drip chamber, hemodialyzer, or directly into a blood circuit line. Preferably, the drip chamber is the point of entry to the blood circuit from the filtrate system.

Moreover, the plasma ultrafiltrate stored in the reservoir is used to flush the blood circuit at the conclusion of the treatment and return blood to the patient. This procedure eliminates the need to use sterile saline at the end of a treatment.

The present invention also encompasses the incorporation of a hemofilter element to the blood circuit of a dialysis system. The hemofilter element accurately removes excess plasma ultrafiltrate or fluid from the patient during dialysis treatment. This fluid accumulates in the patient between treatments due to the underlying kidney disease. The amount of plasma ultrafiltrate removed is controlled by the filtrate pump. Excess fluid accumulation, such as in patients who have concurrent cardiac failure, can lead to hypertension, general edema, and shortness of breath due to fluid accumulation in the lungs. With the incorporation of a hemofilter element in the blood circuit and connected to the filtrate system, the rate and volume of fluid removal can be accurately preset and the volume removed can be stored in the reservoir during treatment, if desired. Further, storage of the ultrafiltrate provides a source of sterile intravenous fluid which can be used to provide fluid to the patient during treatment and to return blood to the patient at the end of the procedure.

The design of the filtrate system permits the introduction or withdrawal of plasma ultrafiltrate from the blood circuit by the manipulation of valves within the filtrate system and by regulation of the direction of plasma ultrafiltrate flow within the filtrate system by the pumping direction of the filtrate pump. The flexible configuration of the filtrate system allows for cleaning, rinsing, and sterilizing agents to be delivered across the hemodialyzer and hemofilter membranes under programmed control of the dialysis system.

The filtrate system can result in controlled fluid removal from the patient during dialysis treatment. For example, when the filtrate pump (68 in FIG. 3) is operated in the "up" direction, plasma ultrafiltrate is pumped into the reservoir (69) from the hemofilter (61). As the ultrafiltrate accumulates in the reservoir (69), the volume is measured by counting the pump shaft revolutions (68) and/or by monitoring the fluid level in the reservoir by electrical, mechanical, or optical means. An example of a mechanical means to monitor fluid level is by a weight balance. Ultrafiltrate removal continues until the determined amount has been removed or the patient displays signs of fluid depletion, at which time the filtrate pump stops.

Should there be a need for replacement fluid, such as during a blood pressure drop or to return the blood to the patient after completion of a dialysis treatment, then the filtrate pump will reverse and operate in the "down" direction. The filtrate pump will operate for a specific number of revolutions to replace a predetermined ultrafiltrate fluid volume to the blood circuit from the reservoir (69) through a pathway leading to the blood circuit. Examples of filtrate-pump-to-blood-circuit pathways include to the hemofilter (the source of the ultrafiltrate), the drip chamber, the hemodialyzer, or directly to a blood circuit line. Preferably, the ultrafiltrate is routed through valve (66) and into the top of the drip chamber (63) or through valve (67) and through the membranes of the hemofilter (61).

The filtrate system also functions to automatically remove accumulated air from the drip chamber. Air is removed from the drip chamber (63) by operating the filtrate pump (68) in the "up" direction with valve (66) open and valve (67) closed. Air is transported to the reservoir (69), where it escapes.

If the hemofilter were not included in the blood circuit, the filtrate system could communicate with the supply line of a hemodialyzer for the dialysate. A valve in the dialysis supply line can direct dialysate through a sterilizing filter and then pump into the filtrate reservoir. The filtered dialysate can be used in the same manner as the ultrafiltrate: to wash the blood circuit, return blood to the patient at the conclusion of a treatment, and to be a fluid source in case of a blood pressure drop.

The filtrate system can control an automated sterilant purge of the filtrate system and blood circuit. For example, the dialysate pump is started and dialysate is pumped through the hemodialyzer, thereby removing sterilant by dialysis. The blood pump is run in the reverse direction through the blood circuit, with the ingress and egress lines shunted together. The filtrate pump is run in the "down" direction (away from the reservoir), with the flow directed to the drip chamber at a flow rate of approximately 50 to 70 ml/min for high-flux dialysis devices. Lower flow rates are used for dialysis devices having lower permeabilities. When air is sensed at the top of the drip chamber, indicating an empty reservoir, the pump is reversed to run in the forward direction (to reservoir), drawing liquid from the hemofilter. This cycle continues until a predetermined volume (e.g., approximately 200 ml) is accumulated in the reservoir. The emptying and filling of the reservoir cycle is continued for about 8 to about 12 cycles, until all sterilant is removed from the entire system.

Further still, the filtrate system can be configured to perform an automated testing of the hemodialyzer and hemofilter membranes. Between dialysis treatments, the membranes of the hemofilter and hemodialyzer are subjected to timed pressure test using air and sterile fluid. The test using air is done to detect leaks in the membrane. The test using fluid is done to analyze membrane permeability. Sterile fluid is obtained by running the dialysate pump forward, and the blood circuit pump runs forward, with the ingress and egress lines connected to form a closed system. The filtrate pump runs "down" (away from the reservoir) at a rate appropriate for the dialyzer being used. The system monitors the pressure required to force the fluid through the membranes at this fixed flow rate. If predetermined upper limits are exceeded, the system will require that the device be replaced by a new one before further processing can continue.

The membrane leakage test utilizes air drawn through a filtered vent at the top of the reservoir. The filtrate pump will draw air from the reservoir and pump it to the filtrate side of the hemofilter and/or hemodialyzer. The air will reach a certain pressure from the filtrate pump, as detected by one or both of the on-line pressure sensors. The pumps are stopped and the pressure is monitored on the pressure sensor for decay for a fixed period of time (e.g., four minutes). "Membrane failure" is defined as an inability to reach the pressure limits or as a rapid rate of pressure decay. For example, in a relatively low permeability dialyzer, a pressure change from 250 mm Hg to 240 mm Hg in four minutes is acceptable for a particular device, whereas a drop to 230 mm Hg is not acceptable. The automated testing procedure determines whether an acceptable level of performance has been established for the next treatment and whether hemofilter or hemodialyzers are leak-free and therefore safe for use. Therefore, the filtrate system, as configured herein, serves as a timesaving device to free the patient from performing the numerous, time-consuming steps required to process contemporary hemodialysis systems.

Accordingly, the configuration of the filtrate system and the ability to automate its function allows for a dialysis system that can automatically self-clean and sterilize after each treatment. Furthermore, the configuration of the filtrate system permits automatic testing of hemodialyzer or hemofilter membrane integrity and permeability.

When the blood circuit contains both a hemofilter and a hemodialyzer, the resulting system can perform hemodiafiltration, which combines high removal rates of low molecular weight substances by diffusion through the hemodialyzer, with high removal rates of higher molecular weight substances by filtration (convection) using the hemofilter. The use of the hemofilter according to the present configuration enables the preparation of sterile fluid from dialysate which can be used as substitution fluid to perform hemofiltration or hemodiafiltration. Preparation of substitution fluid by the inventive system avoids having to purchase and store large quantities of this fluid. Thus, substantial cost and space savings can be achieved by the configuration of the filtrate system in relation to the blood circuit.

Conventional hemodialysis treatment has a drip chamber located downstream from the hemodialyzer to entrap air or gas bubbles, thereby preventing their passage into the patient. The drip chamber is one aspect of the dialysis treatment that is constantly monitored by the patient or the helper. Air accumulated in the drip chamber is manually removed. The presence of a large air to blood surface interface in the drip chamber (2 to 4 cm diameter) develops fibrin rings at the interface. The presence of a hard to clean fibrin ring is a major cause of difficulty in cleaning and reusing the tubing set of the blood circuit.

Yet another aspect of the present invention is its design to automatically detect air in the drip chamber by photo-optical or other sensing means, open the appropriate valve in the filtrate system, and draw out the air from the drip chamber into the filtrate reservoir with the filtrate pump. The direction of pump-regulated flow in the line from the drip chamber to the filtrate reservoir is then reversed and a small amount of ultrafiltrate from the filtrate reservoir is pumped into the drip chamber to purge this transfer line of any residual blood. During the course of this event, hemodialysis proceeds through the blood circuit as normal.

The novel inverted drip chamber design improves the efficiency of air bubble capture, reduces the blood to air interface area, thereby minimizing fibrin ring deposits, and reduces the time that air is present in the drip chamber to further minimize the fibrin ring deposit. There is less opportunity for a fibrin ring depositing in an inverted drip chamber because the upper end is tapered from an inner diameter of approximately 17 mm to the top diameter of the tube of approximately 2 mm, because the air is purged more frequently, and because the drip chamber is the point of heparin (anticoagulant) entry. Normally, from about 1 ml to about 5 ml of volume would be pumped by the filtrate system to purge the inverted drip chamber of air. Therefore, the inverted design of the drip chamber allows both the automated extraction of air and addition of anticoagulant and minimizes the fibrin ring deposit. Accordingly, the tubing set can be cleaned more completely, thereby allowing it to be reused.

The present invention further enables the production of a dialysate from dry chemicals and the ability to automatically vary the individual ionic constituents of the dialysate during treatment. The dry chemicals are formed into a tablet or pellet with an acid or acids, a base or bases and a salt or salts. Preferably, the dry chemical mixture has citric acid as the acid. Preferably, the base and acid are separate or the pellet is made and stored under low humidity conditions. The dry powder is preferably premeasured in the form of a pellet or tablet containing an acid, such as citric acid, separated from a base and a salt. The pelletized dry chemicals are capable of forming dialysates with either acetate-based or bicarbonate-based dialysates without equipment conversion. Preferably, the salt forms a barrier layer between the acid and the base in the tablet or pellet.

The dry chemicals suitable for use include salts comprising an anion and a cation, wherein the anions are selected from the group consisting of bicarbonate, citrate, chloride, acetate, lactate and combinations thereof; and wherein the cations are selected from the group consisting of sodium, potassium, magnesium, calcium, and combinations thereof. Additional organic dry chemicals suitable for use as salts include dextrose and urea. Useful acids include citric acid, lactic acid, ascorbic acid and acetic acid. Typical bases include bicarbonate, carbonate, lactate and citrate. Preferably, sodium, potassium, calcium and magnesium are the cations. One of ordinary skill in the art will know which constituents to use, depending upon a particular patient's condition.

Utilization of discrete tablets or pellets makes it possible to easily change the chemical makeup of the dialysate during treatment in accordance with changing requirements of the individual patient. For example, Raja et al., "Role of Varying Dialysate Sodium and Bicarbonate in the Improvement of Dialysis Vascular Stability," *Prog. Art. Organs*, Nose et al. (eds.), ISAO Press, Cleveland, 1985, pp. 237-39 [Raja et al. I], and Raja et al., "Sequential Changes in Dialysate Sodium (DNa) During Hemodialysis," *Trans. Am. Soc. Artif. Intern. Organs* 29:649-51, 1983 [Raja et al. II] describe several schemes to vary dialysate ion concentrations during treatment. The ability to introduce in prescribed order, pellets with different chemical makeup into the mixing chambers makes possible the timed adjustment in individual dialysate ion concentrations during dialysis treatment in accordance with the prescription of the managing physician. With present equipment, such changes require additional equipment, manual adjustment and recalibration, and affect all ionic species proportionally.

Another example of the benefit of varying the dialysate ion concentration during treatment is to control the rate of osmolar change during dialysis. Several treatment-related symptoms during dialysis have been shown to be related to osmolar decline, and the reduction or blunting in this decline can also reduce treatment symptoms, thus improving the quality of dialysis. One way to achieve this goal is to use sodium modeling. The sodium concentration in the dialysate is increased in the early phase of dialysis and then is slowly reduced to lower concentrations, thus blunting the rate of decline of blood osmolarity. Sodium modeling can only be accomplished, at present, with additional equipment added to a basic dialysis system, and then the procedure is nonselective, altering both sodium and other ions proportionally.

The present invention achieves sodium modeling by loading dry dialysate pellets or tablets with higher sodium concentrations for the early part of dialysis treatment and then gradually using pellets with lower sodium concentrations throughout the remainder of the treatment. Similarly, other osmolar agents, for example urea, can be added.

In present dialysis systems, changing the sodium concentration also proportionally alters the concentrations of other constituents, such as calcium and magnesium. Because individual pellets are introduced at frequent intervals with the inventive system, the concentrations of all ionic species, except those whose change is desired, can be held constant.

The dry dialysate composition is in the form of a dry mixture, pellet or tablet. A dry dialysate composition that will be mixed with one liter of water to form one liter of dialysate comprises from about 130 to about 150 mEq Na, from 0 to about 4.0 mEq of K, from about 2.0 to 3.5 of mEq Ca, from 0 to about 1.5 mEq Mg, from about 25 to about 45 mEq bicarbonate, from 0 to about 2 g glucose, and from about 90 to about 120 mEq chloride ion. Acetate or lactate can be substituted for bicarbonate at the same concentration range. Preferably, citric acid is used at a concentration from about 2 to 12 mEq to maintain an acid pH of the dialysate.

Preferably, the pellets of dry chemicals are added to mix chambers, such as those diagrammed in FIG. 5. Two or more small-volume mixing chambers add the pellets to tap water and pump the solution around to effect a mixing. Each mix chamber can contain from about 2 to about 10 liters of dialysate. Each dialysate chamber volume can be prepared by mixing an appropriate volume of water with a single pellet. The valves located in the pump circuit can switch a mix chamber into a dialysate reservoir to pump dialysate through the dialysate circuit to the hemodialyzer and out to waste. The second mix chamber can be preparing the next reservoir of dialysate for use when the first mix chamber becomes empty. Preferably, there are two mixing chambers.

For example, the use of citric acid in conjunction with conventional dialysate chemicals produces a mixture which will dissolve quickly and completely in the time required by the system. The resulting citrate load is well tolerated, and causes no disturbance of the blood calcium level. Construction of the pellet, such that the more acid components dissolve first, maintains the pH of the solution below the level of 7.40 at all times. This chemical environment prevents the formation of insoluble precipitates, especially calcium salts.

The pellets can be ordered in a pellet dispenser means to change the ion gradient of the dialysate during the treatment process to better suit the individual patient's treatment needs. It is possible to attach a bar code to the pellet and an optical scanner in the means for adding pellets to the mixing chambers to ensure proper gradient formation and to allow the mixing system to adjust monitoring according to pellet composition.

The automated hemodialysis-filtration system can comprise the conventional dialysis system with one, two, three and/or four of the improvements described herein. The improvements include the supply-regulated pump, the filtrate system, including the automated cleaning, testing, sterilization and rinsing steps enabled by the filtrate system, the inverted drip chamber, and/or the dialysate on-line production system. The dialysate on-line production system eliminates the dialysate concentrate and substitutes direct mixing of the dialysate solution from dry chemicals and water.

The following examples are offered by way of illustration and not by way of limitation.

EXAMPLE 1

This example illustrates a comparison of dialysis treatment procedures for conventional dialysis systems and current technology that require patient or helpers to perform all the steps and by the inventive technology that automates most of the manual steps. The inventive technology includes the filtrate system, the supply-regulated pump, the inverted drip chamber, and the dialysate on-line production system. Each treatment is illustrated with a generalized description of the required manual actions, as actual techniques vary widely among treatment facilities. Both methods presume reuse of the hemodialyzer, a practice widely used to reduce the overall cost of treatment. The estimates of patient or helper and total machine time required to complete each task are given.

The following steps are required as preparation for treatment, including start-up, function tests, dialyzer and blood line setup, and the initiation of treatment.

Start-up procedures for conventional dialysis include opening the water supply line valve, filling the reservoir with sufficient liquid dialysate concentrate to complete the treatment (approximately 5 to 6 liters), connecting the concentrate line to the concentrate reservoir, and turning on the machine. Water and dialysate concentrate are proportionately mixed to produce a dialysis fluid of the correct chemical makeup. See U.S. Pat. No. 3,441,136, incorporated by reference herein. The total time for the conventional start-up procedure is 5 to 10 minutes of patient time and 15 to 20 minutes of machine time.

Using an automated system according to the present invention, the start-up procedure includes installing the dialysis pellet cassette on a pellet dispenser (80) and installing the anticoagulant reservoir or anticoagulant pump (70). Both of these actions can be done at any time after the post-treatment processing of the dialysis machine in order to allow timer-activated machine start-up. Next, the machine is turned on (manually or by timer activation). The machine mixes water with the pellets to the correct chemical makeup. The patient time is approximately 1 to 3 minutes, and the machine time is 5 to 10 minutes.

Next, function tests must be performed. In a conventional dialysis system, one must manually and individually test the alarm capabilities of the pressure, blood leak, drip chamber, and conductance monitors. Then one must set monitor limits and sensitivities at desired levels. The patient time is 10 to 15 minutes, and the total time is 10 to 15 minutes.

Using the inventive system, the machine initiates a self-test sequence for all monitors. Patient attendance is not required. After the test sequence is completed, the system reverts to pre-established monitor set points, which may be changed, if desired. The total patient time is 0 minutes and the machine time is approximately 1 to 5 minutes.

Next, the dialyzer and blood lines need to be set up. Using a conventional system, one must perform the following manual steps:

1. Attach new blood lines to hemodialyzer.
2. Place the dialyzer in a holder, arterial end down.
3. Add heparin anticoagulant to a bag of sterile saline.
4. Insert venous drip chamber into the air detector, and the venous line into the occlusion clamp.
5. Attach intravenous fluid administration set between sterile saline bag and end of arterial blood line.
6. Flush arterial blood line with saline.
7. Start dialysate flow through hemodialyzer to remove sterilant from hemodialyzer by dialysis.
8. After sterilant removal from the dialyzer, allow the remainder of the saline to flow into the system, thereby clearing sterilant from the venous blood line.
9. Obtain specimen of effluent saline from end of venous line and test for presence of sterilizing agent.
10. Connect the two monitor lines and adjust air level in drip chambers.
11. Continue flushing, using additional bags of saline until the system is considered to be sterilant-free.

The total patient/helper time is 15 to 20 minutes, and the machine time is 25 to 35 minutes.

Using the inventive system, the dialyzer and blood setup procedure is an automatic sequence which can be initiated and continue without patient/helper participation. The apparatus is prepared for use as follows:

1. The anticoagulant pump operates in the forward direction a sufficient time to purge sterilant from the connecting line between the anticoagulant pump (70) and the drip chamber (63).
2. Dialysate production starts and the blood pump (60) begins to recirculate the contents of the blood circuit.
3. During recirculation, the sterilant is removed from the system by dialysis through the hemodialyzer membranes (62). It is preferred that the fluid flow through the blood circuit be retrograde, venous to arterial, because the sterilant removal is faster. This is because sterilant entering the system from the filtrate reservoir system passes first through the hemodialyzer, where it is removed. If flow is antegrade, sterilant removal can still be achieved but it takes several minutes longer.
4. As dialysis continues and sterilant concentration is reduced, fluid in the filtrate reservoir (69) is emptied into the venous blood line via the drip chamber (63) using the filtrate pump (68).
5. Next, the flow direction of the filtrate pump (68) is reversed and the filtrate reservoir (69) is refilled. This sequence is repeated a predetermined number of times until all the sterilant has been purged from the system. The actual times are adjusted according to the type of hemodialyzer, hemofilter, blood line, and reservoir employed. The patient time is 0 minutes and the machine time is 40 to 70 minutes.

It should be noted that by drawing dialysis fluid across the hemodialyzer membrane into the blood compartment, the inventive system creates its own supply of sterile intravenous fluid (SIVF), which is a physiological solution similar in chemical composition to isotonic saline, commonly used to flush the conventional dialysis circuit, as illustrated herein. By making the SIVF fluid within the inventive system, the cost of purchased saline and other replacement fluids used in dialysis treatment is correspondingly reduced and the inconvenience of their storage and deployment is avoided. SIVF can be made and stored by the system in quantities limited only by the size of the filtrate reservoir (69). The filtrate reservoir (69) is also employed to collect excess fluid which is removed from the patient as part of the therapeutic process. The collected fluids from both the ultrafiltrate and the SIVF may be used during dialysis treatment in several ways. For example, if hypotension (shock) occurs during treatment, necessitating intravenous fluid replacement, SIVF can be used as a replacement intravenous fluid by pumping it from the filtrate reservoir (69) with the filtrate pump (68) through valves (66) and into the blood circuit at the drip chamber (63).

The next step is to initiate treatment. This is accomplished in conventional systems by:

1. Attaching arterial blood lines to hypodermic-type needles previously inserted into the blood vessel.
2. Installing reservoir containing anticoagulant.
3. Starting the anticoagulant pump.
4. Opening the cap on the end of the venous blood line, allowing saline contents of blood tubing to flow out as blood enters the circuit.
5. Removing all clamps from blood lines and turning control knob on blood pump to the 50 to 100 ml/min setting.
6. Checking and adjusting the fluid level in the venous drip chamber.
7. Checking the line pressures before and after the blood pump for indications of an obstruction.
8. Maintaining the pumping rate until the blood appears at the end of the venous blood line, then stopping the blood pump, clamping the venous blood line, and attaching to it a second needle which was previously inserted into a blood vessel.

9. Removing the venous line clamp and manually increasing blood pump flow to desired level.

10. Checking the monitors for excessive pressure.

11. Setting high and low alarm limit on the arterial and venous pressure monitors.

12. Rechecking the blood level in the drip chambers and adjusting as required.

13. Activating the air detector/alarm system at the venous drip chamber.

14. Setting the negative pressure or transmembrane pressure for desired filtrate fluid removal rate.

The total patient time is 20 to 30 minutes, and the total machine time is 20 to 30 minutes.

Using the inventive system, one needs to:

1. Manually or automatically recirculate the contents of the blood compartment for 1 minute, while anticoagulant (e.g., heparin) is introduced.

2. Attach arterial and venous blood lines to needles previously placed in the patient's blood vessels.

3. Remove all clamps from blood lines. Start the blood and anticoagulant pumps and activate all monitors.

4. Blood is then pumped at the optimal rate. Fluid level in the drip chamber is adjusted automatically.

The total patient time is 5 to 10 minutes, and the total machine time is 5 to 10 minutes.

The dialysis treatment is the next procedure in the dialysis process. Using a conventional system and unless changed by the patient or helper, the operating parameters established at the beginning of treatment remain for the duration of the treatment procedure. Blood flow rate and blood circuit pressures are checked by the patient or helper at intervals determined by local protocol, usually every 30 minutes. If any of the monitored parameters change significantly, the typical dialysis machine sounds an alarm to warn of the change. Corrective intervention is usually required by the patient or the helper.

In some systems, intervention may be required to manually alter the dialysate sodium concentration during treatment. This is a preferred practice which seems to reduce the adverse symptoms of treatment, such as muscle cramping and low blood pressure. On conventional dialysis systems offering a sodium change feature, adjustment is accomplished with a control on the dialysate proportioning pump. However, this adjustment changes all dialysate electrolytes in the same ratio as sodium, the sole electrolyte whose change is desired. The total patient and machine times are identical during treatment and vary from 2 to 6 hours.

For treatment using the inventive system, ultrafiltrate fluid is removed from the hemofilter (61) by the filtrate pump (68) through open valve (67) and delivered to the filtrate reservoir (69). If the blood pumping rate is too slow for effective treatment, the system will indicate the likely cause and suggest corrective measures on a display screen, thereby avoiding the need for the patient or the helper to interpret these treatment-related events prior to taking action. The system utilizes information provided by the pump and various pressure sensors located throughout the blood and filtrate circuits to monitor and locate a problem source. By using chemical pellets of desired composition, the precise chemical makeup of the dialysate can be changed according to the direction of the managing physician, with alteration in concentration of only one of the desired constituent electrolytes (e.g., sodium). Proportional changing of all constituents is avoided. For example, the dialysate sodium concentration can be progressively changed from 150 to 135 mEq/L in decrements of 1 or 2 mEq/L during the course of treatment. At the same time, the bicarbonate concentration might be altered from 20 to 35 mEq/L in 5 mEq/L increments during the first 3 hours of the procedure. The dialysate chemical composition can be flexibly changed every few minutes, as each new pellet is introduced, to produce optimal treatment results according to the defined needs of the individual patient. Similarly, the system can be programmed to accurately remove filtrate fluid at either fixed or variable rates. For example, it may be desirable to remove 1 liter of excess fluid from the patient beginning with the second hour of treatment, then to reduce the removal rate to 300 ml/hr for two hours and the rate of fluid removal to individual patient tolerance, thereby reducing adverse side effects.

At the end of the conventional treatment, the patient or helper must first deactivate pressure and air detector alarm systems. Second, the blood pump is turned off. Third, one applies clamps to the arterial blood line and to the attached needle. Fourth, one disconnects tubing from the needle and attaches a saline bag and administers saline to the tubing set. Fifth, one opens the clamp on the blood line and turns the pump on at a reduced rate of flow, thereby returning blood from the blood circuit to the patient. Sixth, when the desired amount of saline has been infused, the pump is turned off and clamps are applied to the lines and then disconnected. The total patient time is 15 to 25 minutes, and the total machine time is 15 to 25 minutes.

Using the inventive system, treatment is discontinued by activating the "discontinue treatment" button. This procedure stops, then reverses the blood pump (60), which begins pumping into the arterial needle at approximately 30 ml/min. Simultaneously, valve (67) opens and the filtrate pump (68) begins to pump SIVF from the filtrate reservoir (69) at approximately 100 ml/min across the hemofilter (61) membrane. This causes SIVF to pass bidirectionally from the hemofilter (61) (retrograde from the arterial line at 30 ml/min and antegrade through the venous line at 70 ml/min), thereby simultaneously returning blood into the patient via both blood lines. When the circuit is clear, clamps are applied to both lines and the circuit is disconnected from the patient. The patient then replaces the pellet cassette with a "sterilizing cassette" to be used to prepare a sterilizing solution as described further. The preferred sterilant is formaldehyde. The total patient time is 10 minutes, and the total machine time is 10 minutes.

Many dialysis systems will reuse as much of the components as possible, especially the hemodialyzer. Using conventional systems, the hemodialyzer is reprocessed by:

1. Detaching and disposing of the blood lines.

2. Removing the hemodialyzer from the machine, placing it in a holder at an open drain, and flushing the blood compartment with tap water for 3 to 5 minutes at 1 to 2 L/min.

3. The water flow is stopped and the water inflow line is disconnected.

4. The dialysate compartment is next flushed with tap water for 3 to 5 minutes at 1 to 2 L/min.

5. Next, the water flow is reestablished through the blood compartment to purge the blood components freed by the previous reverse flush step.

6. The hemodialyzer is tested for usable membrane surface area. To do this, the blood compartment is filled with water, which is then manually purged with pressurized air into a graduated cylinder to measure the blood compartment volume. If the volume has decreased by more than 15 percent from the original volume, the hemodialyzer is discarded, as this signifies a significant loss of perfusable membrane.

7. Membrane leakage is tested by pressurizing the blood compartment with air (approximately 200 mmHg). The hemodialyzer is usually rejected for further use if the pressure drop is more than 4 mmHg/min. If the dialyzer passes both tests, it is filled with sterilant (preferably formaldehyde) and stored for later use. After treatment, the dialysate delivery system is likewise flushed with sterilant by replacing the dialysate concentrate reservoir with a sterilant-containing reservoir and pumping a sterilant and water mixture into the system. The total reuse processing time for the patient is 40 to 60 minutes, and the total machine time is 5 to 10 minutes.

The inventive system uses a different approach to machine and machine component reprocessing. The blood circuit is processed as an integral part of the inventive system. Blood lines, by contrast, are reused. After treatment, water flush is sequentially performed while the entire blood circuit remains on the inventive system. All steps are automated. The two membrane tests are performed in a different fashion. The membrane leakage test is based on the principle that air will pass through a small defect more rapidly than fluid, and therefore is a more sensitive indicator of membrane integrity. For membrane leakage testing, the blood pump is run forward at approximately 200 ml/min. Simultaneously, the filtrate pump (68) draws air through the empty filtrate reservoir (69) and pumps it through valve (67) into the hemofilter (61) jacket until the pressure reaches a prescribed limit (e.g., 250 mmHg). Both pumps stop and the system monitors pressure decay for approximately 4 minutes. Next, air from the same source is directed through valve (66) into the blood circuit via the drip chamber (63) until pressurized to the same level. If pressure decay exceeds limits appropriate to the hemofilter and hemodialyzer being used, the system will so indicate and will not cycle further. "Failure" is defined, for example, as the inability to reach the desired pressure or a rate of pressure decay faster than specified. For example, a pressure change from 250 to 240 mmHg in 4 minutes is acceptable, whereas dropping to approximately 230 mmHg in 4 minutes may not be acceptable.

Instead of using the conventional measure of hemodialyzer blood compartment volume to indicate perfusable membrane surface area as described for the conventional system, the inventive system measures membrane permeability in the hemodialyzer (62) by filling the blood lines with SIVF to a preselected pressure, and then monitoring the pumping rate required to maintain that pressure. This is accomplished by activating the filtrate pump (68), causing SIVF to pass from the filtrate reservoir (69) through valve (66) and into the blood circuit via the drip chamber (63). Filling continues until a predetermined pressure (for example, 250 mmHg) is reached. During the fill, some fluid will have passed across the hemofilter (61) membrane, equalizing the pressure between the hemofilter (61) and the fluid line to valve (67). At this point, fluid can only leave the blood circuit by passing across the hemodialyzer membrane to the dialysate compartment; the faster the rate, the greater the permeability. After pressurization, the inventive system monitors the pumping rate of the filtrate pump (68) required to maintain this pressure. If this rate is below the desired threshold value for the particular hemodialyzer model, membrane permeability is inadequate. The inventive system will so indicate, and discontinue the cycle until the hemodialyzer has been replaced.

A similar test is applied to the hemofilter (61) by opening valve (67) and pressurizing the hemofilter (61) jacket, with filtration occurring from the jacket to the blood compartment of the hemofilter. A pumping rate below the threshold indicates excessive membrane blockage. It should be noted that the hemofilter and hemodialyzer tests also may be performed by pressurizing the system as described herein, then stopping the filtrate pump (68) and monitoring the rate of pressure decay as the indication of membrane permeability of the hemodialyzer and the hemofilter.

When the performance tests have been successfully completed, the system prepares a sterilizing solution (for example, a dialyzable sterilant, such as formaldehyde). The dialysate pellet cassette is removed and replaced with a sterilization cassette. This device consists of a sterilant reservoir and a metering pump for dispensing the sterilant. Where the pellet cassette had a metering gate operated by the host machine, the sterilizing cassette has a mechanical connection to the metering pump. To prepare the sterilizing solution, the host machine operates a metering pump to measure sterilant into the dialysate mixing tank, where it mixes with water to the prescribed strength. The machine senses the correct cassette by means of a mechanical or optical key so that dialysate and sterilant cannot be introduced at the wrong stages of the automated cycle. The sterilant is completely contained within the cassette when not in use, thereby protecting the patient from accidental spills. The sterilant solution is pumped into the dialysate circuit. Simultaneously, the blood pump (60) is activated, recirculating the fluid content of the blood circuit. During recirculation, sterilant is transferred from the dialysate to the blood circuit by reverse dialysis. After the appropriate sterilant concentration is achieved within the blood circuit, the filtrate pump (68) is activated, drawing the sterilant through the hemofilter jacket (61) and the open valve (67) into the filtrate reservoir. With pump (68) still operating, valve (67) closes and valve (66) opens, causing sterilant to fill the line between the drip chamber (63) and the filtrate pump (68). During this final step, the anticoagulant pump (70) is activated to withdraw sterilant from the line between the drip chamber (63) and the filtrate pump (68), thereby sterilizing the anticoagulant line. The system then proceeds to a standby mode until reactivated. The total patient time is from 1 to 3 minutes, and the total machine time is from 30 to 60 minutes.

EXAMPLE 2

This example illustrates the response of the conventional dialysis system and the inventive system that contains the filtrate system to a drop in blood pressure. A common occurrence during conventional hemodialysis is a drop in blood pressure resulting in a shock-like condition. This is typically corrected, in conventional systems, by starting an intravenous saline drip. If shock is severe, the patient is unable to perform this action by him/herself. This risk is one of the principal causes of patient anxiety and why patients depend upon a helper.

The inventive system uses available blood pressure monitoring equipment, for example, from Physio Control Corporation to monitor blood pressure at predetermined intervals, for example, every 5 minutes. By using such instrumentation during treatment with the inventive filtrate system, a new level of safety and convenience can be achieved for the patient. The blood pressure monitor is programmed to send a signal to the machine when blood pressure falls to an undesirable level (for example, a drop in systolic pressure to below 90 mmHg in some patients, which may be different for each patient). This signal stops ultrafiltrate fluid removal and may initiate a fluid replacement sequence.

The fluid replacement sequence has valve (66) opening, allowing the filtrate pump (68) to deliver a predetermined quantity of replacement fluid from the filtrate reservoir (69) to the blood circuit via the drip chamber (63), thereby increasing patient blood volume. Additional fluid may be delivered at preset intervals until blood pressure returns to the desired level.

EXAMPLE 3

It is also possible for the patient to electively introduce known volumes of replacement fluid into the blood circuit when certain symptoms occur. For example, a patient may be feeling faint, reflecting a decreased blood volume and the beginning of a shock-like condition. It is also known that some symptoms experienced by patients during treatment, such as cramps and headache, may diminish when small fluid volumes are administered. The ability to self-administer replacement fluid from the filtrate reservoir (69), as described in Example 2 above, reduces patient symptoms and enhances the patient's well being and quality of treatment.

EXAMPLE 4

This example illustrates testing we have done to demonstrate successful operation of the filtrate system and successful operation of the air extraction system. A dialysis system blood circuit was constructed using an inverted drip chamber and a filtrate system as illustrated in FIG. 3. A three liter blood bag was used for the plasma ultrafiltrate reservoir. A standard hemofilter, hemodialyzer and blood pump were used. Commercially available valves and pressure sensors were employed. This system was successfully tested by manual cycling.

The dialysis system was attached to a 110 lb sheep as a model for a patient. The sheep was dialyzed on several occasions to test for system function. The entire operating sequence, beginning with attachment of the blood lines to the blood access and ending with a blood return to the patient/sheep, was performed. The hemodialysis process used the filtrate system to withdraw an ultrafiltrate from the hemofilter, collect it in the filtrate reservoir, and at the end of treatment, used the stored ultrafiltrate for bi-directional blood flushing from the blood circuit.

During the dialysis treatment of the sheep, air was introduced into the blood lines and observed to collect at the top of the inverted drip chamber. Activation of the air removal system resulted in transfer of this air from the drip chamber to the filtrate reservoir. Similarly, ultrafiltrate from the reservoir was effectively transferred into the drip chamber when needed during the dialysis treatment. These studies demonstrate that the air removal system works satisfactorily and that an ultrafiltrate can be collected in the filtrate reservoir and returned to the blood circuit as required.

The anticoagulant, heparin, was introduced into the blood circuit via the inverted drip chamber. The rapid elimination of air from the top of the drip chamber combined with the drip chamber as the site of anticoagulant administration into the blood circuit, completely prevented any formation of a fibrin ring that usually forms in the drip chamber.

In summary, a hemodialysis-filtration system including a blood circuit, an air extraction system and the filtrate system, as described herein, were used to perform hemodialysis treatments on a sheep. During these treatments, the inventive air extraction system in the inventive filtrate system, anticoagulant administration via the inverted drip chamber and ultrafiltrate withdrawal and return were demonstrated to work successfully.

EXAMPLE 5

This example illustrates the membrane testing procedures required for automated hemofilter processing and reuse by the inventive hemodialysis-filtration system. It is common practice in kidney dialysis treatment centers and in dialysis patient homes to clean and reuse hemodialyzers. There is, however, minimal experience with multiple reuse of hemofilters. In particular, there are no criteria or standards for gauging hemofilter membrane safety and efficacy after processing and before use again on patients.

We developed and evaluated two methods of testing hemofilter performance which are suited to automated usage in the inventive hemodialysis-filtration system in general and the inventive filtrate system in particular. These automated test methods assess hemofilter membrane permeability following chemical cleaning of the hemofilter, and also evaluate membrane integrity, the presence or absence of hemofilter membrane leaks.

Cleaning effectiveness (membrane permeability) was measured by recirculating cleaning agent through the hollow fiber hemofilter, measuring inlet (arterial) pressure, and recording the time required for this pressure to drop to its lowest stable level. Cleaning agents used were sodium hydroxide, sodium hypochlorite, hydrogen peroxide and pepsin. The preferred agent was (0.5%) sodium hypochlorite which cleaned a typical hollow fiber hemofilter in approximately 40 minutes. The test system employed and a graph of test results are shown in FIGS. 5 and 6. These tests were performed on Amicon Diafilter ® 30, Renaflow ® HF 400, Ultraflux ® AV600 and Hemoflow ® F60 hemofilters. Acceptance or rejection of cleaned hemofilters for further use would be based on a comparison of measured transmembrane pressures with pressure standards established for that device.

Tests of membrane integrity were conducted on Amicon Diafilter ® 30 and Hemoflow ® F60 hemofilters, and on Travenol ® 1211 hemodialyzers. We punctured a single fiber in each hollow fiber device by tearing or snagging the fiber with a fine wire under a microscope. The fiber device with the defective fiber was subject to air pressure on one side of the membrane. Air pressure was employed instead of fluid hydraulic pressure because air will pass through a small membrane defect more rapidly than fluid, thereby producing faster pressure drop and hence greater sensitivity to membrane faults. In all cases the air pressure could not be raised to 200 mm Hg. This pressure loss is well in excess of pressure losses acceptable for hollow fiber hemofilters and hemodialyzers presently in use. Accordingly, this test illustrates the proposed use of pressurized air to identify defective hemofilter and hemodialyzer membranes even with minor membrane damage.

EXAMPLE 6

This example illustrates the safety and efficacy of a citrate-containing dialysate. The initial feasibility testing of compressed chemical dialysate pellets, indicated that their solubility was dependent upon the acidity of the resulting dialysate solution. Citric acid was selected to maintain the pH in the region of 7.1 to 7.2. Citric acid is available in powdered form and is easily converted in the body into physiological bicarbonate. We ran a series of sheep experiments to study the biological safety of using citric acid to acidify the dialysate. The sheep were dialysed against a dialysate produced with the dry chemical system, as described herein, containing 3.5 mEq/L citric acid. The chemical composition of the dialysate was evaluated to ensure that the dialysate composition contained the proper pH and the correct amount of each of the dialysate ions. The major concern in using a citric acid-based dialysate was the citrate load delivered to the patient (sheep). Citrate is known to bind ionized calcium, thus making calcium unavailable for use by the body. The ionized calcium and citrate levels in the sheep blood stream were measured during and after a five-hour dialysis treatment.

Ionized calcium levels increased during dialysis treatment from 2.34 mEq/L to 2.85 mEq/L, indicating that the citrate was not decreasing the ionized calcium level. The blood levels of citrate increased to a plateau of 0.115 mmol/L after three to four hours of dialysis treatment, and then returned to the baseline level within one hour after the completion of dialysis treatment. The plateau concentration (0.115 mmol/L) is approximately 20% of the concentration normally used to anticoagulate blood. Therefore, it is concluded that the blood calcium measurements obtained while using the citrate-containing dialysate demonstrate that the pelletized system produces dialysate which is as safe for use as dialysate made with current conventional methods.

EXAMPLE 7

This example illustrates the use and benefits of the supply-regulated pump. The supply-regulated pump was constructed as described herein using several different materials to form the chamber. The materials used included polyvinyl chloride, polyurethane, and silicone rubber. Silicone rubber was used for more extensive testing.

We constructed a prototype single-chamber supply-regulated blood pump and used a silicone rubber chamber and connecting tubes. The supply-regulated pump was set up to pump water at 200 ml/min in an open loop, and subjected to continuous operation for 24 hours a day. The pump operated within the speed specifications and without a tubing failure for over 2000 hours. This is equivalent to over two years of dialysis treatments. A conventional roller pump would have required multiple changes of pump tubing for 2000 hours of pumping.

The supply-regulated blood pump was set up to pump blood from a sheep. The blood was pumped successfully at a rate based upon the supply from the sheep. During the tests, the blood supply to the pump was reduced by restricting the connection line between the sheep and the pump chamber inlet. In all such instances, the pumping rate slowed until the restriction was cleared.

The pump tests also showed that abrupt changes in chamber internal dimensions can produce zones of disturbed and stagnant blood flow which lead to clot and fibrin formation. Based upon these observations, the pump chambers were redesigned to provide gradual dimensional changes. The testing of the revised chambers by pumping blood to and from sheep showed that clotting was eliminated.

From the foregoing, it will be appreciated that, although specific embodiments of the invention have been described herein for purposes of illustration, various modifications may be made without deviating from the spirit and scope of the invention.

What is claimed is:

1. A dry dialysate composition comprising an acid, bicarbonate and a salt, where the acid is separated from the bicarbonate, wherein the acid will dissolve first in an aqueous solution and the bicarbonate will dissolve after solution of the acid, and where said composition upon mixing with water forms a solution comprising from about 2 to about 12 mEq/L of the acid, from about 25 to about 45 mEq/L of the bicarbonate, and from about 1.5 to about 150 mEq/L of the salt.

2. The dry dialysate composition of claim 1 wherein the acid is citric acid.

3. The dry dialysate composition of claim 1 wherein, upon dissolving in water, the pH is about 7.0 to below 7.4

4. A dry dialysate composition comprising bicarbonate, acetate, lactate or combinations thereof, sodium, calcium, chloride, citric acid, and optionally potassium, magnesium, and glucose, wherein said composition, upon mixing with water, forms a solution comprising:
   from about 130 to about 150 mEq/L of sodium ion;
   from about 0 to about 4.0 mEq/L of potassium ion;
   from about 2.0 to about 3.5 mEq/L of calcium ion;
   from about 0 to about 1.5 mEq/L of magnesium ion;
   from about 25 to about 45 mEq/L of bicarbonate ion;
   acetate, lactate or combinations thereof;
   from about 0 to about 2.0% glucose;
   from about 90 to about 120 mEq/L of chloride ion; and
   from about 2 to about 12 mEq/L of citric acid.

5. A dry dialysate composition comprising an acid, a base and a salt wherein the acid is selected from the group consisting of citric acid, lactic acid, ascorbic acid, acetic acid and combinations thereof, wherein the base is selected from the group consisting of bicarbonate, carbonate, lactate, citrate and combinations thereof, and where said composition upon mixing with water forms a solution comprising from about 2 to about 12 mEq/L of the acid, from about 25 to about 45 mEq/L of the base, and from about 1.5 to about 150 mEq/L of the salt.

6. A dry dialysate composition comprising bicarbonate, acetate, lactate or combinations thereof, sodium, calcium, chloride, and citric acid, wherein said composition, upon mixing with water, forms a solution comprising:
   from about 130 to about 150 mEq/L of sodium ion;
   from about 2.0 to about 3.5 mEq/L of calcium ion;
   from about 35 to about 45 mEq/L of bicarbonate ion;
   acetate, lactate or combinations thereof;

from about 90 to about 120 mEq/L of chloride ion; and from about 2 to about 12 mEq/L of citric acid.

7. A dry dialysate composition comprising an acid, a base and a salt wherein the acid is selected from the group consisting of citric acid, ascorbic acid and combinations thereof, wherein the base is selected from the group consisting of bicarbonate, carbonate, lactate, citrate and combinations thereof, and where said composition upon mixing with water forms a solution comprising from about 2 to about 12 mEq/L of the acid, from about 25 to about 45 mEq/L of the base, and from about 1.5 to about 150 mEq/L of the salt.

* * * * *

UNITED STATES PATENT AND TRADEMARK OFFICE
CERTIFICATE OF CORRECTION

PATENT NO. : 5,252,213
DATED : October 12, 1993
INVENTOR(S) : Suhail Ahmad et al It is certified that error appears in the above-indentified patent and that said Letters Patent is hereby corrected as shown below:

In column 26, claim 6, line 67, please delete "35" and substitute therefor --25--.

Signed and Sealed this

Fifth Day of April, 1994

Attest:

BRUCE LEHMAN

*Attesting Officer*     *Commissioner of Patents and Trademarks*